United States Patent [19]
Baker

[11] Patent Number: 4,554,686
[45] Date of Patent: Nov. 26, 1985

[54] POLYMETHYLMETHACRYLATE BONE CEMENTS AND METHODS FOR PREPARING SUCH BONE CEMENTS

[75] Inventor: Charles D. Baker, Lehi, Utah

[73] Assignee: Technical Research Associates, Inc., Salt Lake City, Utah

[21] Appl. No.: 584,605

[22] Filed: Feb. 29, 1984

[51] Int. Cl.$^4$ .......................... A61F 1/00; B05D 3/06; C08F 6/02

[52] U.S. Cl. ........................................ 623/16; 623/10; 128/92 R; 427/398.1; 427/2; 523/307; 528/481

[58] Field of Search .................... 3/1.91, 1.911, 1.912, 3/1.913; 427/398.1; 128/92 R; 523/117, 116, 115, 114, 113, 307; 528/481

[56] References Cited

U.S. PATENT DOCUMENTS

| 4,246,210 | 1/1981 | Wilson et al. | 523/307 X |
| 4,283,799 | 8/1981 | Pratt, Jr. et al. | 3/1.913 |
| 4,307,472 | 12/1981 | Morris | 3/1.913 X |
| 4,336,618 | 6/1982 | Raab | 3/1.913 |

OTHER PUBLICATIONS

Zimmer Technical Report on Zimmer Bone Cement, Sep., 1977.

Primary Examiner—Richard J. Apley
Assistant Examiner—A. Cannon
Attorney, Agent, or Firm—Workman, Nydegger & Jensen

[57] ABSTRACT

The present invention is directed to polymethylmethacrylate bone cement that is premixed and frozen so as to arrest the polymerization reaction at a suitable point. The frozen bone cement is treated by electromagnetic radiation to insure sterility. In use, the bone cement is warmed until it reaches a temperature and consistency suitable for use. The bone cement may be prepackaged in a syringe, or may be molded for use in connection with a particular prosthesis, or may be packaged unitarily with a prosthesis.

41 Claims, No Drawings

POLYMETHYLMETHACRYLATE BONE CEMENTS AND METHODS FOR PREPARING SUCH BONE CEMENTS

BACKGROUND

1. Field of the Invention

The present invention is related to improved bone cements and methods for preparing such bone cements. More particularly, the present invention is directed to improved polymethylmethacrylate bone cements for securing metal and plastic prostheses to bone and to the methods of preparing such bone cements.

2. The Prior Art

Surgical procedures to reconstruct or repair bones have become extremely common. For instance, a variety of prostheses are commercially available for use in repairing damaged hip joints or knee joints due to such diseases as osteoarthritis, rheumatoid arthritis, traumatic arthritis, avascular necrosis, and sickle cell anemia osteoporosis. In these procedures, the prosthesis is typically cemented in place by use of a polymethylmethacrylate bone cement.

Polymethylmethacrylate is a self-curing acrylic resin; it polymerizes at room temperature without any external application of heat. Polymethylmethacrylate bone cement comes to the surgeon in a kit form consisting of two components that must be mixed together to initiate polymerization.

The first component is a liquid mixture comprising monomeric methyl methacrylate together with a small amount of N, N-dimethyl-p-toluidine to induce setting of the mixed cement, and hydroquinone to inhibit self-polymerization of the monomer liquid. The second kit component is a polymer powder including polymethylmethacrylate. Frequently, the radiopaque compound barium sulfate is also included in the powder component to serve as an opacifier, and some commercial formulations include benzoyl peroxide as a catalyst to the polymerization reaction. Some commercial compositions of polymer powder also include substantial amounts of methylmethacrylate-styrene copolymer; this copolymer is believed to improve the mixing qualities of the cement.

Polymethylmethacrylate is a "luting" agent, rather than an adhesive; this cement does not produce any chemical bond with bone tissue to hold the prosthesis in place, but rather fills irregularities in the bone and hardens to form a mechanical interlock.

Because only a mechanical bond is involved, technique is extremely important. Failure to achieve a firm bond results in eventual loosening of the prosthesis; this, in turn, typically results in extreme discomfort to the patient, and a need for surgical replacement of the prosthesis.

The most often-used technique for reconstructing damaged bone tissue involves initially preparing the bone tissue by cutting and drilling the bone tissue so that it conforms to the shape of the securement portion of a prosthesis. Then, a number of shallow holes are generally drilled or cut into the surfaces of the bone tissue adjacent to the prosthesis in order to form projecting cavities into which cement will flow so as to form a strong mechanical interlock between the bone cement and the bone tissue.

The prepared bone surfaces are then thoroughly cleansed of all blood, fatty marrow tissue, bone fragments, and the like, so that the cement will conform to all of the surface irregularities of the prepared bone tissue. Finally, the two components of the unpolymerized bone cement are mixed.

The recommended manner of mixing the cement involves emptying the powdered component into a sterile mixing bowl followed by addition of the liquid component. The two components are then subjected to thorough mixing for about one minute until the commencement of polymerization is observed. Then, the cement can be loaded into a syringe while still quite fluid for injection into the prepared area. Alternatively, the cement can be kneaded for about another minute until it becomes dough-like, and then it is formed into a suitable shape for placement in the attachment site.

Once mixing of the bone cement is commenced, it is critical that the surgeon act quickly; the polymethylmethacrylate bone cement sets up extremely rapidly, and unless it is used quickly it will not flow into the irregularities and projecting cavities within the prepared bone tissue. Typically, it takes about two (2) minutes to prepare the cement for use, and the cement becomes too viscous to produce a reliable bond if it is not used within about five (5) or six (6) minutes.

Thus, the surgeon generally has only about three (3) or four (4) minutes within which to place the cement and prosthesis into the prepared reconstruction site. Even then, the bond is generally stronger if the cement and prosthesis are placed into the prepared site early within this time period rather than later. The earlier the cement is applied, the more fluid it is, and the more likely that it will flow into surface irregularities and projecting cavities. The prosthesis is then held in proper position by the surgeon for several more minutes while the cement continues to harden.

It will be appreciated that the need for haste is extremely disadvantageous. As the bone cement continues to harden, a delay of only seconds might mean the difference between success and failure. A host of occurrences, such as the need to further cleanse the prepared bone tissue, or a fluctuation in the patient's vital signs, or failure of the surgeon or his assistants to work quickly enough, can easily cause precious time to be lost. Unfortunately, the success or failure of the procedure is learned only later when the bond fails because of poor mechanical attachment to the bone tissue.

Further, the requirement for haste is not conducive to good sterile technique. Infection at the attachment site can result in damage to the restored joint, and infection can also require additional surgery to avoid further complications. Accordingly, the avoidance of infection at the site of the restoration is just as important as the obtaining of a good mechanical bond; hence, it is critical that the cement be maintained in sterile condition. Yet, the requirement to open two packages, to mix their contents, to position the cement and then the prothesis, and to do it all within just a few minutes leads to significant difficulties in maintaining good sterile technique. The result is that there is a significant likelihood of introducing infection into the surgical site.

Difficulties caused by the need for haste are not the only factors that relate to whether the prosthesis will be permanently secured. Even in those cases where a surgeon implants the prothesis within five or six minutes from commencement of mixing, there is no guarantee of success.

Because the cement comes in convenient preweighed and measured amounts, many surgeons assume that following a standard procedure will result in a cement that sets up in exactly the same manner in every case.

However, minor variations in the ratio of powder to liquid, variations in ambient temperature (taking into account such factors as nearness of surgical lights, whether the cement is kneaded with the hands, and the patient's body temperature), and variations in the size and shape of the cement mass to be placed all have important effects of the rate of polymerization. Thus, in some cases, polymerization occurs more rapidly than expected so that the cement is too viscous for reliable use even prior to five minutes from commencement of mixing.

In addition to the problems associated with conventional bone cements mentioned above, working with the various components of bone cement can be hazardous to the health of the individuals involved in its preparation and use. For instance, the liquid monomer is a highly volatile substance and is known to be irritating to the respiratory tract, eyes, and the liver. Since as much as 15% of the liquid monomer evaporates during the mixing step, the concentration of monomer vapor in the vicinity of the person doing the mixing can be high enough to cause injury. This is particularly true over prolonged periods of time due to the cumulative effects where the same person mixes batch after batch of the bone cement in operation after operation.

The liquid monomer component is also a very powerful lipid solvent, and it is known to cause contact dermatitis. Although it is recommended that those persons having direct contact with the cement wear several pairs of surgical gloves to minimize absorption into their bodies, this caution is frequently not observed. Even where it is observed, this precaution does not entirely block all absorption of the monomer into their hands, and long-term damage remains a significant possibility.

In addition to hazards to operating room personnel, the use of bone cement also frequently causes injury to the patient's bone tissue. For instance, the polymerization reaction is highly exothermic, and the temperature of the cement can climb to as much as 110° C. during the polymerization process. Temperatures in the range of 70° C. to 80° C. are common.

One frequent source of failure of the prosthetic reconstruction is due to tissue necrosis at the bone-cement interface; a thin fibrous layer often forms at the interface between the cement and bone, and this tissue sometimes results in so much loosening of the prothesis that a second surgical operation is required.

Because of the foregoing problems, some surgeons have attempted to entirely avoid the use of bone cement by devising other mechanical attachment methods. Moreover, a great deal of effort and expense has been directed at attempts to provide such improved attachment methods. Other research has been directed to the development of improved bone cement formulations. However, these attempts have proved largely unavailing, and most surgeons continue to utilize polymethylmethacrylate in the maner described above, despite the serious problems connected with its use.

From the foregoing, it will be appreciated that it would be a significant advancement in the art of securing prostheses to bone by use of polymethylmethacrylate bone cement to provide methods and apparatus capable of extending the time available to a surgeon preparatory to placing the cement and prosthesis. It would also be a significant advancement if the hazards to operating room personnel due to the toxicity of constituents of uncured polymethylmethacrylate could be alleviated. It would also be very significant if improved sterile techniques could be provided for preparing the cement for placement, and if tissue necrosis at the bone-cement interface due to high temperatures could be reduced. It would further be a significant advancement if cement could be mixed in a manner that led to more predictable and reproducible results. Such advancements in the art are described and claimed herein.

BRIEF SUMMARY AND OBJECTS OF THE INVENTION

The present invention is directed to methods and apparatus relating to the use of polymethylmethacrylate bone cement in the reconstruction of damaged bone tissue. In accordance with the present invention, damaged bone tissue is prepared to accept a suitable prosthetic device, which is secured in place by use of bone cement that had been premixed, but frozen to arrest polymerization.

Use of premixed frozen bone cement avoids the need to mix the bone cement in the operating room, thereby freeing surgical assistants for other tasks, and eliminating the health hazard associated with such mixing. The lower temperatures involved also extend the time available to the surgeon within which to place the bone cement. By permitting the premixed bone cement to be prepared under controlled manufacturing conditions, the frozen bone cement will have a predictable consistency and composition that will maximize the probability of a successful reconstruction operation. Moreover, preparation of the bone cement in a carefully controlled manner substantially decreases the likelihood of harmful effects to operating room personnel from long-term exposure to bone cement.

Another feature of the present invention is the ability to sterilize the premixed bone cement while in frozen form by treatment with suitable electromagnetic radiation, such as gamma radiation from a cobalt-60 source. Such sterilization minimizes the likelihood of introducing infection into the restoration site.

It is, therefore, a primary object of the present invention to provide methods and apparatus for extending the time available to a surgeon during bone reconstruction surgical procedures within which to place bone cement and an associated prosthesis.

It is another object of the present invention to provide methods and apparatus that minimize health hazards to operating room personnel occasioned by use of polymethylmethacrylate bone cement.

Yet another object of the present invention is to provide methods and apparatus that minimize the extent of damage to the patient's bone tissue resulting from the heat generated by bone cement as it cures.

Still a further object of the present invention is to provide methods and apparatus that insure the sterility of bone cement used in reconstruction surgical procedures.

Yet a further object of the present invention is to provide methods and apparatus for preparing bone cement having a reproducible consistency, composition, and properties.

These and other objects and features of the present invention will become more fully apparent from the following description and appended claims.

DETAILED DESCRIPTION OF THE INVENTION

The present invention provides methods and apparatus that avoid many of the problems inherent in conventional use of polymethylmethacrylate bone cement to secure surgical prostheses to living bone.

As mentioned above, once bone cement has been mixed, the surgeon typically has only about three to four minutes within which to properly place the bone cement and the prosthesis before the cement becomes so viscous that it is incapable of forming a reliable mechanical bond with the bone tissue. One feature of the present invention is the extension of the amount of time the surgeon has within which to place the cement and prosthesis, and the corresponding termination of the need for haste in this phase of the reconstruction procedure.

These benefits are obtained by providing the bone cement to the surgeon in a different form than that of conventional practice. Thus, in accordance with the present invention, rather than providing the surgeon with cement components that must be prepared in the operating room for use, the surgeon is provided with premixed cement that has been quick-frozen to temporarily halt the polymerization reaction.

It is possible to halt the polymerization reaction at virtually any point along the polymerization process. Thus, polymerization can be permitted to progress to a point that is optimum for a particular purpose, and then the bone cement may be rapidly frozen to arrest the polymerization reaction at precisely that point. Because the mixing of the bone cement that is to be frozen for later use can be conducted under controlled conditions, it is possible to insure that virtually every portion of frozen bone cement is substantially identical to every other portion in terms of composition and extent of polymerization. This removes yet one more variable encountered by the surgeon, thereby greatly improving the likelihood of a successful reconstruction.

Another significant advantage of premixing the bone cement in controlled conditions is the improved ability to provide sterile bone cement under those conditions. Thus, the manufacturing process can be specifically designed for production of bone cement; this is in marked contrast to the conventional situation wherein the mixing step is merely one activity among many in a busy operating room.

As a result, the mixing process can be arranged in a manner most conducive to preparation of bone cement. The mechanization of the mixing process would by itself assist greatly in improving the quality and sterility of bone cement. Further, a technician responsible for mixing the bone cement under controlled conditions will become especially proficient in mixing bone cement so as to conform to desired standards, including standards of sterility.

As indicated above, the polymerization reaction can be stopped at virtually any selected point by subjecting the bone cement to rapid freezing. It has been discovered that such freezing does not adversely affect the polymethylmethacrylate bone cement, and such cement will resume polymerization upon warming.

Because of its low expense and ready availability, it is preferred that liquid nitrogen be utilized to effect rapid freezing of the partially polymerized bone cement. Liquid nitrogen is extremely advantageous for this purpose because of its low temperature, and also because of its being in a liquid form that readily conforms to the outline of the bone cement and quickly conducts heat from the bone cement. In practice, the bone cement may simply be dropped into a container of liquid nitrogen and left until the liquid nitrogen ceases to "boil"; at this point the cement will be completely frozen.

It will be appreciated that other materials can be used to effect freezing of the bone cement in lieu of liquid nitrogen. However, it is preferred that such a material be capable of reducing the temperature of the bone cement to the point where polymerization is arrested within about ten to fifteen seconds.

It has been discovered that bone cement may be stored for extended periods at temperatures warmer than liquid nitrogen temperatures. For instance, frozen polymethylmethacrylate bone cement can be stored indefinitely at dry ice temperatures (about $-80°$ C.). This greatly facilitates shipment of frozen bone cement, and also raises the temperature of the bone cement closer to its melting temperature (about $-5°$ C.), thereby reducing the extent of warming necessary to resume polymerization. It has also been found that partially polymerized polymethylmethacrylate bone cement can be stored at conventional freezer temperatures ($-70°$ C.) for extended periods. In contrast, it has been found that at a higher temperature of about $-30°$ C., a significant amount of polymerization occurs over extended periods making long-term storage of frozen bone cement at this temperature undesirable.

As mentioned above, the act of mixing the bone cement under controlled manufacturing conditions greatly facilitates good sterile technique. However, it has been discovered that frozen bone cement may be subjected to gamma radiation, such as from a Cobalt-60 source, or to an electron beam, to virtually guarantee sterile conditions. Thus, it has been found that bone cement held at a temperature between about $-50°$ C. and $-135°$ C. can be sterilized by irradiation with gamma radiation without undergoing any substantial degree of polymerization. At temperatures below about $-135°$ C., gamma radiation is ineffective to effect sterilization because bacterial spores become biologically inert below that temperature. The effectiveness of gamma radiation as a sterilization agent increases as the temperature of the frozen bone cement is raised. However, as the temperature is raised above about $-50°$ C., significant amounts of polymerization are induced during sterilization. Accordingly, it is preferred that sterilization by gamma ray radiation be effected at temperatures below about $-50°$ C. It is feasible to premix bone cement with clean rather than sterile technique, and using components that have not been previously sterilized, and yet insure sterility of the bone cement supplied to the surgeon.

In connection with existing prior art bone cements, the powder component of unmixed bone cement is generally sterilized by gamma irradiation, but because the monomer will degrade if subjected to gamma radiation, the monomer liquid is generally sterilized by filtration through a bacterial filter. The subjection of frozen premixed bone cement to gamma radiation could avoid the need to subject the monomer liquid to sterilization on a bacterial filter.

Because the premixed bone cement can be frozen at virtually any stage in the polymerization process, it is possible to provide bone cement having suitable characteristics for any particular application. For instance, in those types of reconstruction procedures where it is preferred to inject semi-liquid bone cement into a restoration site by means of a syringe, it is possible to freeze the premixed bone cement before any substantial amount of polymerization has occurred. Advantageously, the bone cement may be loaded into a syringe or syringe cartridge before freezing, thereby avoiding the need for additional handling by the surgeon or his assistants.

Alternatively, the bone cement can be permitted to undergo a further degree of polymerization before being frozen. For instance, the premixed bone cement can be taken into the "dough" state before being frozen. It will be appreciated that other alternatives are also available.

In use, the frozen bone cement is withdrawn from a freezer in the operating room (typically maintained at about $-70°$ C.) after the restoration site has been prepared and cleansed. It has been found that the premixed bone cement is a good thermal conductor, and rapidly warms to the point where polymerization recommences. Once polymerization recommences, the heat generated by that exothermic process assists in warming the bone cement to the point where it becomes malleable. Typically, frozen bone cement can be warmed in the hands of the surgeon (wearing surgical gloves) from freezer temperatures to the point where it is ready for use in only about one or two minutes.

As explained above, one disadvantage of current techniques involving bone cement is the frequent occurrence of bone tissue necrosis due to the heat generated by the polymerizing bone cement. The present invention substantially avoids this adverse event in two ways. First, the heat generated prior to the point where the premixed bone cement is frozen is completely removed from the system. Thus, only that amount of heat that is generated after resumption of polymerization is of concern, and this factor alone can result in a substantial temperature reduction at the cement-bone tissue interface.

Second, the bone cement will generally be placed into the restoration site while it is still rather cool; heat initially generated by the polymerization reaction is used in warming the bone cement up to room temperature. Since only a particular amount of heat is generated by a particular mixture of bone cement, yet further decreases will be observed in the maximum temperature reached within the reconstruction site at the bone cement-bone tissue interface.

As indicated above, an important feature of the present invention is avoidance of the requirement for undue haste in the operating room. Even as the polymerization reaction recommences upon warming, it is initially much slower than the normal polymerization rate at room temperature. Then, because the temperature of the mixture remains lower throughout the process than is observed at corresponding conditions of polymerization in connection with conventional use of bone cement, there is a significantly extended period of time between thawing of the cement to the point where it may be used, until the bone cement becomes too viscous for reliable use. By increasing the period within which the cement is capable of forming a reliable bond, the likelihood of success of the reconstruction is substantially increased.

The use of frozen bone cement is also advantageous because it eliminates the primary health hazard to operating room personnel—breathing of the monomer vapor during the mixing step in the operating room.

Further, by providing the bone cement to the surgeon in a form already polymerized to the desired extent, there is little or no need for handling by the physician other than to mold it to a desired shape and to effect placement. Thus, the dangers of contact dermatitis which are associated with prior art bone cements are avoided. Another feature of the present invention is the ability to provide bone cement in preformed condition that will conform to a typical bone preparation and corresponding prosthesis. It is quite practical to mold premixed bone cement in the laboratory prior to freezing. Thus, the surgeon using premolded frozen bone cement need only place the warmed cement into position in the reconstruction site without any significant handling of the material. This procedure not only increases the likelihood of successful attachment of the prothesis, but it also minimizes handling of the bone cement.

It will be appreciated that for many surgical procedures it will be advantageous to sell the bone cement and the associated prosthesis as a unit, with the frozen bone cement already secured to the prosthesis. For instance, the molded bone cement can be frozen and then mounted on the prosthesis, or the premixed cement can be molded around the prosthesis while curing, and then both the cement and prosthesis subjected to temperatures sufficient to freeze the bone cement and arrest the polymerization reaction.

From the foregoing, it will be appreciated that the present invention for the first time presents the surgeon with bone cement that will have characteristics that are reproducible from batch to batch. No longer will variations in mixing technique, or differences in mixing time cause variations in the rate and the extent of polymerization of the cement placed into a reconstruction site. No longer will the surgeon be subjected to the requirement for undue haste from the moment he orders the cement mixed, wherein he must insure that the cement is mixed, molded, and installed together with the prosthesis in the reconstruction site, all within no more than five to six minutes.

Rather, in accordance with the present invention, the surgeon can order removal of frozen premixed bone cement from the freezer, knowing that it will have the proper consistency. Further, short delays will not result in the bone cement becoming too viscous for use, since the lower temperatures involved slow down the rate of polymerization, thereby substantially increasing the time available to the surgeon within which to place the bone cement in the desired location.

The present invention is also safer for operating room personnel than conventional techniques since no substantial amounts of monomeric liquid are permitted to evaporate into the air, and since the amount of handling by the surgeon and assistants is minimized. Use of frozen bone cement is safer to the patient because there is significantly less probability of introducing an infection with the bone cement, and because the likelihood and extent of bone tissue necrosis due to high temperatures of polymerization is significantly lessened.

The present invention may be embodied in other specific forms without departing from its spirit or essential characteristics. The foregoing description is to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for preparing polymethylmethacrylate bone cement for use in attaching a surgical prosthesis to prepared bone tissue, the method comprising the steps of:

mixing a bone cement composition including methylmethacrylate with a composition capable of initiating a polymerization of the methylmethacrylate;

blending the bone cement composition until a desired degree of partial polymerization has occurred;

placing substantially free flowing partially polymerized bone cement into syringe means;

freezing the partially polymerized bone cement in order to substantially arrest polymerization of the methylmethacrylate in the bone cement composition;

irradiating the frozen bone cement with suitable electromagnetic radiation capable of sterilizing the frozen bone cement without inducing substantial amounts of polymerization of the methylmethacrylate in the frozen bone cement; and storing the sterilized, frozen bone cement at a temperature below about −70° C. until use of the bone cement.

2. A method for preparing polymethylmethacrylate bone cement as defined in claim 1, wherein the freezing step is accomplished by placing the partially polymerized bone cement into freezing means capable of effecting rapid freezing of the bone cement.

3. A method for preparing polymethylmethacrylate bone cement as defined in claim 2, wherein said rapid freezing of the bone cement is effected in less than about 15 seconds.

4. A method for preparing polymethylmethacrylate bone cement as defined in claim 1, wherein the freezing step is accomplished by submerging the partially polymerized bone cement in liquid nitrogen.

5. A method for preparing polymethylmethacrylate bone cement for use in attaching a surgical prosthesis to prepared bone tissue, the method comprising the steps of:

mixing a bone cement composition including methylmethacrylate with a composition capable of initiating a polymerization of the methylmethacrylate;

blending the bone cement composition until a desired degree of partial polymerization has occurred;

forming the partially polymerized bone cement into a suitable shape for use with a particular surgical prosthesis;

freezing the partially polymerized bone cement in order to substantially arrest polymerization of the methylmethacrylate in the bone cement composition;

irradiating the frozen bone cement with suitable electromagnetic radiation capable of sterilizing the frozen bone cement without inducing substantial amounts of polymerization of the methylmethacrylate in the frozen bone cement; and storing the sterilized, frozen bone cement at a temperature below about −70° C. until use of the bone cement.

6. A method for preparing polymethylmethacrylate bone cement for use in attaching a surgical prosthesis to prepared bone tissue, the method comprising the steps of:

mixing a bone cement composition including methylmethacrylate with a composition capable of initiating a polymerization of the methylmethacrylate;

blending the bone cement composition until a desired degree of partial polymerization has occurred;

forming the partially polymerized bone cement onto a surgical prosthesis;

freezing the partially polymerized bone cement while formed on the surgical prosthesis in order to substantially arrest polymerization of the methylmethacrylate in the bone cement composition;

irradiating the frozen bone cement and prosthesis with suitable electromagnetic radiation capable of sterilizing the frozen bone cement and the prosthesis without inducing substantial amounts of polymerization of the methylmethacrylate in the frozen bone cement; and storing the sterilized, frozen bone cement and prosthesis at a temperature below about −70° C. until use of the bone cement.

7. A method for preparing polymethylmethacrylate bone cement for use in attaching a surgical prosthesis to prepared bone tissue, the method comprising the steps of:

mixing a bone cement composition including methylmethacrylate with a composition capable of initiating a polymerization of the methylmethacrylate;

blending the bone cement composition until a desired degree of partial polymerization has occurred;

freezing the partially polymerized bone cement in order to substantially arrest polymerization of the methylmethacrylate in the bone cement composition;

irradiating the frozen bone cement with suitable electromagnetic radiation capable of sterilizing the frozen bone cement without inducing substantial amounts of polymerization of the methylmethacrylate in the frozen bone cement; and storing the sterilized, frozen bone cement at a temperature below about −70° C. until use of the bone cement;

warming the frozen bone cement to a temperature suitable to permit it to be used to attach a surgical prosthesis to prepared bone tissue.

8. A method for preparing polymethylmethacrylate bone cement as defined in claim 1, wherein the electromagnetic radiation is gamma radiation.

9. A method for preparing polymethylmethacrylate bone cement as defined in claim 8, wherein the gamma radiation is from a cobalt-60 source.

10. A method for preparing polymethylmethacrylate bone cement as defined in claim 8, wherein the frozen bone cement is maintained at a temperature below about −50° C. during irradiation by gamma radiation.

11. A method for preparing polymethylmethacrylate bone cement as defined in claim 1, wherein the electromagnetic radiation is an electron beam.

12. A method for preparing polymethylmethacrylate bone cement as defined in claim 2, further comprising the step of placing the frozen bone cement into temperature maintenance means adapted to maintain the bone cement at a temperature wherein no substantial amount of polymerization occurs.

13. A sterile frozen bone cement composition including methylmethacrylate and suitable polymerization initiating agents wherein polymerization has been initiated but arrested at a desired degree of partial polymerization, said partially polymerized bone cement composition being placed into syringe means while in a substantially free-flowing condition and then frozen while in said syringe means, and wherein the frozen partially polymerized bone cement in the syringe is maintained at a temperature below about −70° C. until use.

14. A sterile frozen bone cement composition including methylmethacrylate and suitable polymerization initiating agents wherein polymerization has been initiated but arrested at a desired degree of partial polymerization, said partially polymerized bone cement composition being formed into a suitable shape for use with a particular surgical prosthesis and then frozen, and wherein the partially polymerized bone cement is maintained at a temperature below about −70° C. until use.

15. A sterile frozen bone cement composition including methylmethacrylate and suitable polymerization initiating agents wherein polymerization has been initiated but arrested at a desired degree of partial polymerization, said partially polymerized bone cement composition being formed on a surgical prosthesis and frozen while secured to said prosthesis, and wherein the partially polymerized bone cement is maintained at a temperature below about −70° C. until use.

16. A bone prosthesis for use in the repair of damaged bone tissue comprising a suitable prothesis; and preformed sterile frozen bone cement secured thereto in a manner such that the prothesis and bone cement may be unitarily placed into prepared bone tissue to effect repair thereof, said frozen bone cement being partially polymerized, but having polymerization thereof arrested at a desired degree of polymerization.

17. A bone prosthesis as defined in claim 16, wherein the prosthesis and associated bone cement are maintained at a temperature below about −70° C. prior to use.

18. A method for preparing polymethylmethacrylate bone cement as defined in claim 5 wherein the freezing step is accomplished by placing the partially polymerized bone cement into freezing means capable of effecting rapid freezing of the bone cement.

19. A method for preparing polymethylmethacrylate bone cement as defined in claim 18, wherein said rapid freezing of the bone cement is effected in less than about 15 seconds.

20. A method for preparing polymethylmethacrylate bone cement as defined in claim 5, wherein the freezing step is accomplished by submerging the partially polymerized bone cement in liquid nitrogen.

21. A method for preparing polymethylmethacrylate bone cement as defined in claim 5, wherein the electromagnetic radiation is gamma radiation.

22. A method for preparing polymethylmethacrylate bone cement as defined in claim 21, wherein the gamma radiation is from a cobalt-60 source.

23. A method for preparing polymethylmethacrylate bone cement as defined in claim 21, wherein the frozen bone cement is maintained at a temperature below about −50° C. during irradiation by gamma radiation.

24. A method for preparing polymethylmethacrylate bone cement as defined in claim 5, wherein the electromagnetic radiation is an electron beam.

25. A method for preparing polymethylmethacrylate bone cement as defined in claim 18, further comprising the step of placing the frozen bone cement into temperature maintenance means adapted to maintain the bone cement at a temperature wherein no substantial amount of polymerization occurs.

26. A method for preparing polymethylmethacrylate bone cement as defined in claim 6 wherein the freezing step is accomplished by placing the partially polymerized bone cement into freezing means capable of effecting rapid freezing of the bone cement.

27. A method for preparing polymethylmethacrylate bone cement as defined in claim 26, wherein said rapid freezing of the bone cement is effected in less than about 15 seconds.

28. A method for preparing polymethylmethacrylate bone cement as defined in claim 6, wherein the freezing step is accomplished by submerging the partially polymerized bone cement in liquid nitrogen.

29. A method for preparing polymethylmethacrylate bone cement as defined in claim 6, wherein the electromagnetic radiation is gamma radiation.

30. A method for preparing polymethylmethacrylate bone cement as defined in claim 29, wherein the gamma radiation is from a cobalt-60 source.

31. A method for preparing polymethylmethacrylate bone cement as defined in claim 29, wherein the frozen bone cement is maintained at a temperature below about −50° C. during irradiation by gamma radiation.

32. A method for preparing polymethylmethacrylate bone cement as defined in claim 6, wherein the electromagnetic radiation is an electron beam.

33. A method for preparing polymethylmethacrylate bone cement as defined in claim 26, further comprising the step of placing the frozen bone cement into temperature maintenance means adapted to maintain the bone cement at a temperature wherein no substantial amount of polymerization occurs.

34. A method for preparing polymethylmethacrylate bone cement as defined in claim 7 wherein the freezing step is accomplished by placing the partially polymerized bone cement into freezing means capable of effecting rapid freezing of the bone cement.

35. A method for preparing polymethylmethacrylate bone cement as defined in claim 34, wherein said rapid freezing of the bone cement is effected in less than about 15 seconds.

36. A method for preparing polymethylmethacrylate bone cement as defined in claim 7, wherein the freezing step is accomplished by submerging the partially polymerized bone cement in liquid nitrogen.

37. A method for preparing polymethylmethacrylate bone cement as defined in claim 7, wherein the electromagnetic radiation is gamma radiatioin.

38. A method for preparing polymethylmethacrylate bone cement as defined in claim 37, wherein the gamma radiation is from a cobalt-60 source.

39. A method for preparing polymethylmethacrylate bone cement as defined in claim 37, wherein the frozen bone cement is maintained at a temperature below about −50° C. during irradiation by gamma radiation.

40. A method for preparing polymethylmethacrylate bone cement as defined in claim 7, wherein the electromagnetic radiation is an electron beam.

41. A method for preparing polymethylmethacrylate bone cement as defined in claim 34, further comprising the step of placing the frozen bone cement into temperature maintenance means adapted to maintain the bone cement at a temperature wherein no substantial amount of polymerization occurs.

* * * * *